United States Patent
Bachar

(10) Patent No.: US 10,478,283 B2
(45) Date of Patent: Nov. 19, 2019

(54) DILATING DEVICE FOR PROSTATIC URETHRA

(71) Applicant: Butterfly Medical Ltd., Yokneam Yilit (IL)

(72) Inventor: Yehuda Bachar, Givaat Shmuel (IL)

(73) Assignee: BUTTERFLY MEDICAL LTD., Yorkneam Yilit (IL)

( * ) Notice: Subject to any disclaimer, the term of this patent is extended or adjusted under 35 U.S.C. 154(b) by 95 days.

(21) Appl. No.: 15/114,107

(22) PCT Filed: Jan. 26, 2015

(86) PCT No.: PCT/IL2015/050092
§ 371 (c)(1),
(2) Date: Jul. 26, 2016

(87) PCT Pub. No.: WO2015/111063
PCT Pub. Date: Jul. 30, 2015

(65) Prior Publication Data
US 2017/0000598 A1    Jan. 5, 2017

Related U.S. Application Data

(60) Provisional application No. 61/931,645, filed on Jan. 26, 2014.

(51) Int. Cl.
| | | |
|---|---|---|
| A61F 2/04 | (2013.01) | |
| A61F 2/966 | (2013.01) | |
| A61B 18/00 | (2006.01) | |

(52) U.S. Cl.
CPC ............... *A61F 2/04* (2013.01); *A61F 2/042* (2013.01); *A61F 2/966* (2013.01);
(Continued)

(58) Field of Classification Search
CPC .... A61F 2/04; A61F 2/042; A61F 2/86; A61F 2002/047; A61B 2018/00517
See application file for complete search history.

(56) References Cited

U.S. PATENT DOCUMENTS

| | | |
|---|---|---|
| 5,269,802 A | 12/1993 | Garber |
| 5,496,365 A | 3/1996 | Sgro |
| (Continued) | | |

FOREIGN PATENT DOCUMENTS

| | | |
|---|---|---|
| WO | 2010/073244 A2 | 7/2010 |
| WO | 2015/101975 A1 | 7/2015 |
| WO | 2015/111063 A1 | 7/2015 |

OTHER PUBLICATIONS

May 11, 2016 International Search Report issued in International Patent Application No. PCT/IB2015/055731.
(Continued)

*Primary Examiner* — Dinah Baria

(57) ABSTRACT

A dilating device for the prostatic urethra comprising: at least three, laterally connected ridges, wherein each ridge is configured to longitudinally engage with a different substantially longitudinal groove of the prostatic urethra of a patient, and wherein the at least three laterally connected ridges are configured to laterally compress to enable insertion into the prostatic urethra in a compressed configuration, and wherein the at least three laterally connected ridges are configured to laterally expand to a normally-open configuration upon deployment within the prostatic urethra, to exert a radially outwards force that dilates the prostatic urethra.

16 Claims, 8 Drawing Sheets

(52) U.S. Cl.
  CPC .............. *A61B 2018/00517* (2013.01); *A61F 2002/047* (2013.01); *A61F 2220/0008* (2013.01); *A61F 2230/0006* (2013.01); *A61F 2230/0095* (2013.01)

(56) References Cited

U.S. PATENT DOCUMENTS

| | | | |
|---|---|---|---|
| 6,994,093 B2 * | 2/2006 | Murphy | A61B 17/0218 128/898 |
| 8,591,569 B2 | 11/2013 | Shin et al. | |
| 8,603,187 B2 | 12/2013 | Kilemnick et al. | |
| 2003/0040803 A1 | 2/2003 | Rioux et al. | |
| 2003/0069647 A1 | 4/2003 | Desmond, III et al. | |
| 2004/0167635 A1 | 8/2004 | Yachia et al. | |
| 2011/0276081 A1 * | 11/2011 | Kilemnik | A61B 17/320725 606/198 |

OTHER PUBLICATIONS

May 31, 2015 International Search Report issued in International Patent Application No. PCT/IL2015/050092.

* cited by examiner

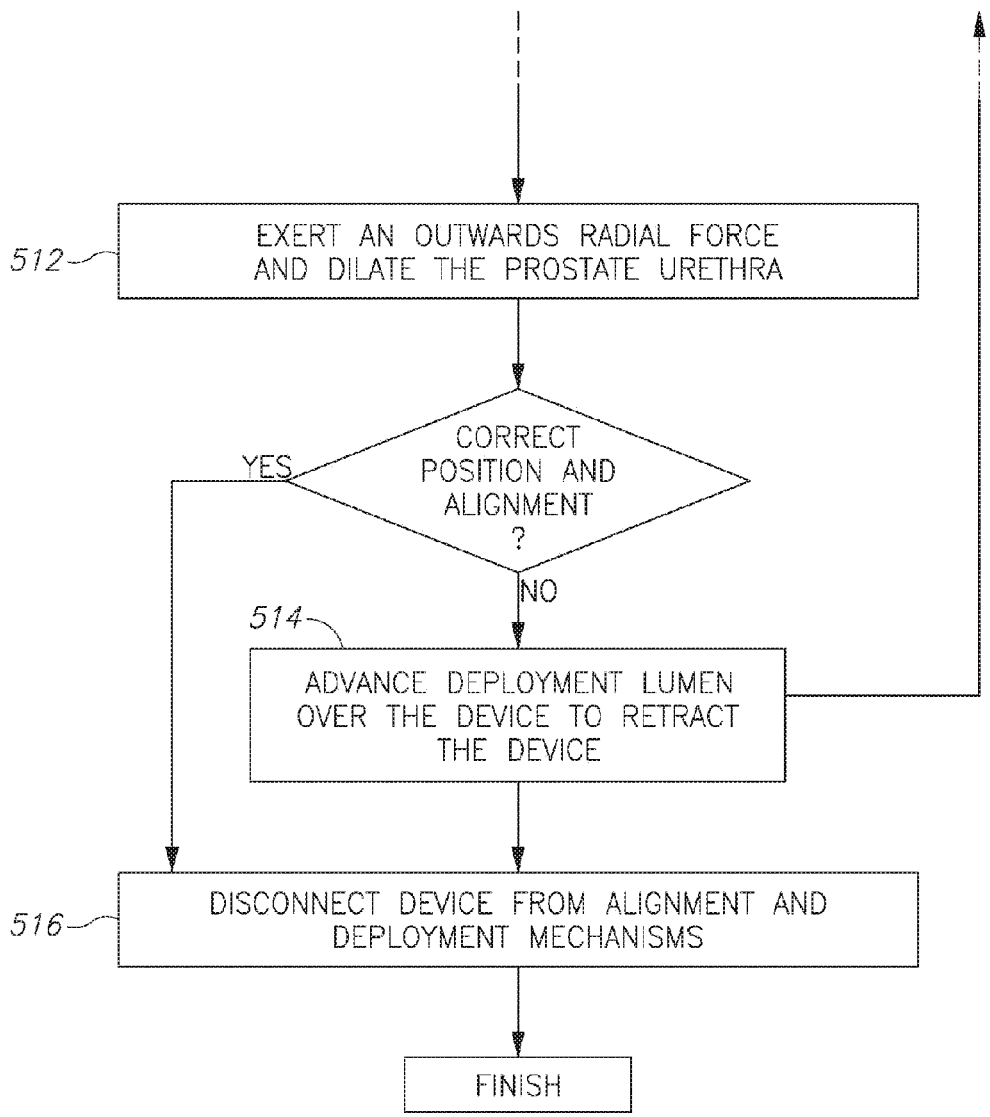
FIG.5 (cont. 1)

DILATING DEVICE FOR PROSTATIC URETHRA

CROSS REFERENCE TO RELATED APPLICATIONS

This application is a U.S. National Stage Entry Under 35 U.S.C. 371 of International Application No. PCT/IL2015/050092 filed on Jan. 26, 2015, which claims the benefit of priority under 35 USC § 119(e) from U.S. Provisional Patent Application No. 61/931,645, filed on Jan. 26, 2014 and entitled "A Dilating Device For Prostatic Urethra". The contents of the above applications are incorporated herein by reference in their entireties.

FIELD OF THE INVENTION

The invention relates to the field of urological medical devices.

BACKGROUND

Benign prostate hyperplasia (BPH), also known as benign prostatic hypertrophy, is a urological disease in which the prostate enlarges and constricts the urethra. BPH affects a majority of the male population over 50 years of age, and is thus of great medical and commercial importance.

Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). However, surgical treatment is an extremely invasive procedure which is debilitating, painful and often traumatic to the patient. Various complications including impotence, incontinence, bleeding, infection and other undesirable problems attendant with such surgery can result.

Another procedure to treat prostatic hypertrophy is to place a catheter at the external opening of the urethra and into the obstructed portions of the urethra, allowing urine to pass from the bladder by way of the catheter lumen. These urinary catheters typically employ a positioning or retention balloon at the distal tip which inflates at the bladder neck and prevents the expulsion of the catheter from the body.

Heat, such as produced by microwave or laser energy, may be provided in combination with such catheters for treating the enlarged portion of the prostate. However, this procedure may result in pain and discomfort to the patient The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a dilating device for the prostatic urethra, the device comprising: at least three, laterally connected longitudinal ridges, wherein each ridge is configured to longitudinally engage with a different substantially longitudinally groove of the prostatic urethra of a patient, and wherein the at least three laterally connected ridges are configured to laterally compress to enable insertion into the prostatic urethra in a compressed configuration, and wherein the at least three laterally connected ridges are configured to laterally expand to a normally-open configuration upon deployment within the prostatic urethra, to exert a radially outwards force that dilates the prostatic urethra.

In some embodiments, the at least three laterally connected ridges comprise two peripheral ridges that are each configured to engage with a different postero-lateral groove of the prostatic urethra, and a central ridge that is configured to engage with the anterior inter-lobar groove of the prostatic urethra.

In some embodiments, there is further provided one or more connectors that laterally connect each peripheral ridge to the central ridge.

In some embodiments, the one or more connectors laterally connect each peripheral ridge to the central ridge at a point on each ridge that lies between the distal and proximal ends of the peripheral and central ridges.

In some embodiments, the one or more connectors comprise two distal connectors that laterally connect a distal end of each peripheral ridge to a distal end of the central ridge, and two proximal connectors that laterally connect a proximal end of each peripheral ridge to a proximal end of the central ridge, thereby forming two closed forms joined at the central ridge.

In some embodiments, the two closed forms comprise lengthwise oriented ovoid loops that together form a figure-eight shape in the normally-open configuration.

In some embodiments, the two closed forms form two substantially rectangular shapes that span two substantially non-parallel planes in the normally-open configuration.

In some embodiments, the two distal connectors are substantially S-shaped, and are configured to span a portion of a cylinder in the normally-open configuration, thereby dilating the prostatic urethra at the bladder neck.

In some embodiments, the two proximal connectors are substantially S-shaped, forming a butterfly shape by the device in the normally-open configuration.

In some embodiments, all the at least three laterally connected ridges and one or more connectors are configured to maintain intimate contact with the prostate urethra mucosa.

In some embodiments, there is further provided two or more distally positioned protrusions that are configured to impinge against the postero-lateral side of the bladder neck, thereby preventing a migration of the device into the urinary bladder.

In some embodiments, the at least three laterally connected ridges are composed of wire.

In some embodiments, the at least three laterally connected ridges are composed of cut foil.

In some embodiments, the at least three laterally connected ridges are composed of super-elastic alloy.

In some embodiments, the at least three laterally connected ridges are composed of super-elastic polymer.

In some embodiments, the super-elastic polymer is a biodegradable polymer.

In some embodiments, the device is configured to allow free passage of a liquid when deployed in the prostatic urethra.

In some embodiments, the shape of the device is configured to reside within the prostate urethra.

In some embodiments, the at least three, laterally connected ridges are further configured to: laterally compress for fitting within a deployment lumen, laterally expand to a normally-open configuration upon extraction from the deployment lumen, and exert the outwards radial force upon deployment within the prostatic urethra.

In some embodiments, the deployment lumen is configured to be housed within a work channel of a cystoscope.

In some embodiments, the deployment lumen is further provided with a fluid delivery lumen and balloon that are configured to deliver a fluid to the bladder to allow deploying the device within the prostatic urethra via the bladder.

In some embodiments, the at least three, laterally connected ridges are provided with one or more proximally disposed protrusion that are configured to releasably connect the device to an alignment mechanism housed within the deployment lumen.

In some embodiments, the alignment mechanism comprises a releasable string that loops through the protrusions and runs through an alignment lumen.

In some embodiments, the device is configured for alignment within the prostatic urethra via a torque that is transferred from the alignment mechanism.

There is provided, in accordance with an embodiment, a method for dilating a prostatic urethra, the method comprising: inserting a dilating device into the urethra of a patient; aligning the dilating device within the prostatic urethra; positioning the dilating device within the prostatic urethra of the patient; and deploying the dilating device within the prostatic urethra, thereby causing the dilating device to: expand to a normally-open configuration, engage with the grooves of the prostatic urethra, exert a radially outwards force on the prostatic urethra, and dilate the prostatic urethra.

In some embodiments, positioning comprises extracting the device from a deployment lumen and inserting the device into the urinary bladder of the patient.

In some embodiments, positioning comprises drawing the device from the bladder into the prostate urethra.

In some embodiments, aligning comprises transferring a torque applied to an alignment mechanism connected to the device.

In some embodiments, the torque is applied by rotating an alignment lumen that is connected to the device.

In some embodiments, aligning comprises positioning a central ridge of the device for engaging with the anterior inter-lobar groove of the prostatic urethra and positioning two peripheral ridges of the device to each engage with a different postero-lateral groove of the prostatic urethra.

In some embodiments, the method further comprises causing the device to laterally compress and retreat within the deployment lumen if the alignment or position of the device is incorrect.

In some embodiments, the method further comprises causing the device to impinge against the postero-lateral side of the bladder neck, thereby preventing a migration of the device into the urinary bladder.

In some embodiments, the method further comprises disconnecting the device from a deployment lumen provided to deploy the device.

In some embodiments, the method further comprises applying a positioning balloon to secure the position of the deployed device.

There is provided, in accordance with an embodiment, a kit for dilating a prostatic urethra, the kit comprising: a deployment lumen; and a dilating device which comprises: at least three, laterally connected ridges, wherein each ridge is configured to vertically engage with a different substantially vertical groove of the prostatic urethra of a patient, and wherein the at least three laterally connected ridges are configured to laterally compress to enable insertion into the prostatic urethra, in a compressed configuration, through said deployment lumen, and wherein the at least three laterally connected ridges are configured to laterally expand to a normally-open configuration upon deployment from said deployment lumen into the prostatic urethra, to exert a radially outwards force that dilates the prostatic urethra.

In some embodiments, the at least three, laterally connected ridges are provided with one or more proximally disposed protrusion that are configured to releasably connect the device to an alignment mechanism housed within the deployment lumen.

In some embodiments, the alignment mechanism comprises a releasable string that loops through the protrusions and runs through an alignment lumen.

In some embodiments, the device is configured for alignment within the prostatic urethra via a torque that is transferred from the alignment mechanism.

In some embodiments, the deployment lumen is configured to be housed within a work channel of a cystoscope.

In some embodiments, the deployment lumen is further provided with a balloon that is configured to position the device within the within the prostatic urethra.

In some embodiments, the at least three laterally connected ridges comprise two peripheral ridges that are each configured to engage with a different postero-lateral groove of the prostatic urethra, and a central ridge that is configured to engage with the anterior inter-lobar groove of the prostatic urethra.

In some embodiments, the kit further comprises one or more connectors that laterally connect each peripheral ridge to the central ridge.

In some embodiments, the one or more connectors laterally connect each peripheral ridge to the central ridge at a point on each ridge that lies between the distal and proximal ends of the peripheral and central ridges.

In some embodiments, the one or more connectors comprise two distal connectors that laterally connect a distal end of each peripheral ridge to a distal end of the central ridge, and two proximal connectors that laterally connect a proximal end of each peripheral ridge to a proximal end of the central ridge, thereby forming two closed forms joined at the central ridge.

In some embodiments, the two closed forms comprise lengthwise oriented ovoid loops that together form a figure-eight shape in the normally-open configuration.

In some embodiments, the two closed forms form two substantially rectangular shapes that span two substantially non-parallel planes in the normally-open configuration.

In some embodiments, the two distal connectors are substantially S-shaped, and are configured to span a portion of a cylinder in the normally-open configuration, thereby dilating the prostatic urethra at the bladder neck.

In some embodiments, the two proximal connectors are substantially S-shaped, forming a butterfly shape by the device in the normally-open configuration.

In some embodiments, all the at least three laterally connected ridges and one or more connectors are configured to maintain intimate contact with the prostate urethra mucosa.

In some embodiments, the kit further comprises two distally positioned protrusion that are configured to impinge against the postero-lateral side of the bladder neck, thereby preventing a migration of the device into the urinary bladder.

In some embodiments, the at least three laterally connected ridges are composed of wire.

In some embodiments, the at least three laterally connected ridges are composed of cut foil.

In some embodiments, the at least three laterally connected ridges are composed of super-elastic alloy.

In some embodiments, the at least three laterally connected ridges are composed of super-elastic polymer.

In some embodiments, the super-elastic polymer is a biodegradable polymer.

In some embodiments, the device is configured to allow free passage of a liquid when deployed in the prostatic urethra.

There is provided, in accordance with an embodiment, a dilating device for the prostatic urethra, the device comprising: at least two dilating means of the prostate urethra, wherein the dilating means are connected by ridges that are configured to fix the dilating means in place within the prostate urethra and prevent their movements or dislodgement and wherein the dilating means are configured to laterally expand to a normally-open configuration upon deployment within the prostatic urethra, to exert a lateral outwards force that dilates the prostatic urethra.

In some embodiments, the dilating means comprise arcs that exert lateral forces on the lateral lobes.

In some embodiments, the dilating means comprise rings.

In some embodiments, the shape of the device in a normally open configuration is configured to reside within a delimiting surface of a longitudinally oriented tube.

In some embodiments, the device is shaped to reside within the prostate urethra.

In some embodiments, the dilating means and connecting ridges of the device are configured to maintain intimate contact with the prostate urethra mucosa.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1A:
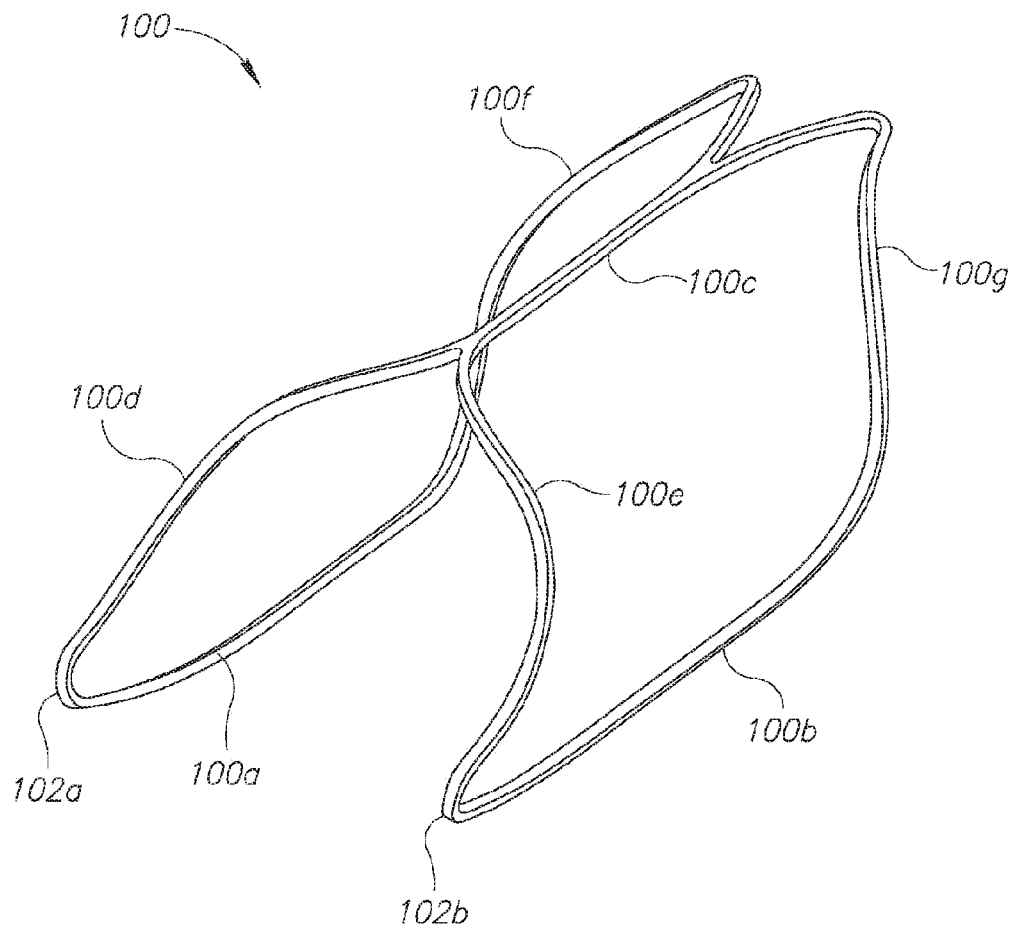
FIG. 1A-B illustrates a dilating device for the prostatic urethra from a perspective view and a top view, respectively, in accordance with an embodiment.

Disclosed herein is a device that is configured to dilate the prostatic urethra by engaging with the three grooves of the prostatic urethra and exerting a radially outwards force upon deployment within the urethra. The device may be normally open, and made of a resilient material allowing it to laterally compress for fitting within a deployment lumen, and to laterally expand to a normally-open configuration upon extraction from the deployment lumen, and exert the outwards radial force that dilates the prostatic urethra upon deployment.

FIGS. 1 through 5, wherein like parts are designated by like reference numerals throughout, illustrate a dilating device for the prostatic urethra, and a method of use according to the present invention. Although the present invention will be described with reference to the figures, it should be understood that many alternative forms can embody the present invention. One of ordinary skill in the art will additionally appreciate different ways to alter the parameters disclosed, such as the size, shape, or type of elements or materials, in a manner still in keeping with the spirit and scope of the present invention.

Figure 1B:
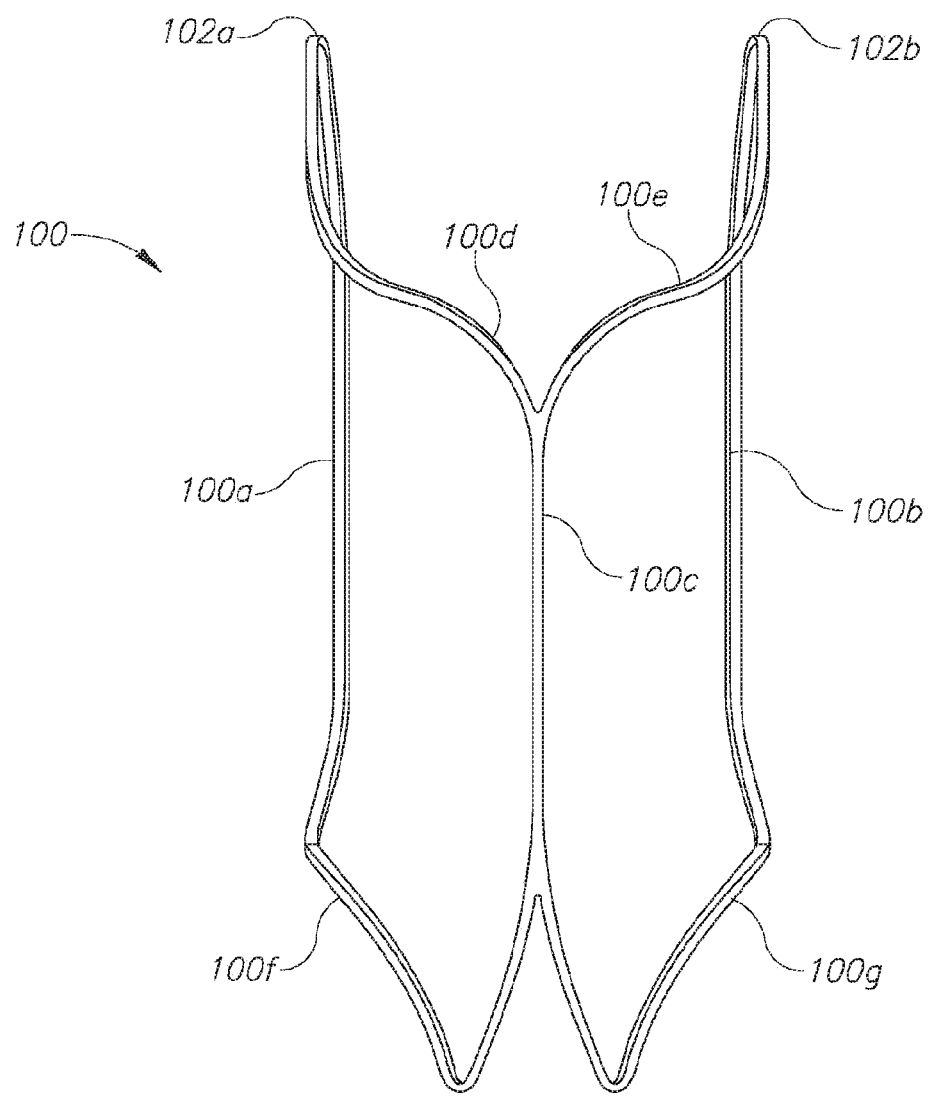

Reference is now made to FIGS. 1A-B which illustrates a dilating device 100 for the prostatic urethra, from a perspective view and a top view, respectively, in accordance with an embodiment. Device 100 may comprise at least three laterally connected ridges 100a, 100b, 100c, each of which is configured to longitudinally engage with a different substantially longitudinal groove of the prostatic urethra of a patient. Device 100 may be normally-open, and may be configured to laterally compress, causing the distance between ridges 100a, 100b, 100c to decrease, thereby enabling the insertion of device 100 into the prostatic urethra in a compressed configuration, and to laterally expand to its normally-open configuration, causing the distance between ridges 100a, 100b, 100c to increase, upon deployment within the prostatic urethra. The lateral expansion of device 100 when deployed within the prostatic urethra may exert a radially outward force that causes ridges 100a, 100b, 100c to engage with the grooves of the urethra and push them outwards, thereby dilating the prostatic urethra, and allowing a free flow of a liquid, such as urine, to pass from the bladder through the urethra and out of the patient's body.

Peripheral ridges 100a, 100b may each be configured to engage with a different postero-lateral groove of the prostatic urethra, and central ridge 100c may be configured to engage with the anterior inter-lobar groove of the prostatic urethra.

Two distal connectors 100d, 100e may branch out from a V-shaped distal end of central ridge 100c and laterally connect to the distal ends of peripheral ridges 100a and 100b, respectively. Additionally, two proximal 100f, 100g may branch out from a proximal end of central ridge 100c and laterally connect to the proximal ends of peripheral ridges 100a, and 100b, thereby forming two closed forms that are joined at central ridge 100c. In one embodiment, proximal connectors 100f and 100g may branch out from a V-shaped proximal end of central ridge 100c, as illustrated in FIG. 1A. In the embodiment of FIG. 1A, connectors 100d, 100e, 100f, and 100g may be substantially S-shaped, forming a butterfly shape by device 100 when in the normally-open configuration, where proximal connectors 100f, and 100g may be configured for positioning towards the distal end of the prostate urethra.

Device 100 may be provided with two, or more distally positioned protrusions 102a and 102b that are configured to impinge against the postero-lateral side of the bladder neck, and prevent a migration of device 100 into the urinary bladder. Protrusions 102a and 102b may be integrally formed with distal connectors 100d, 100e, such as forming a portion of the S-shape of distal connectors 100d, 100e that are shown in FIGS. 1A, 2.

Device 100 may additionally be configured for alignment within the prostatic urethra via two proximally disposed protrusions 104a and 104b that are provided with device 100 to releasably connect device 100 to an alignment mechanism provided with the deployment lumen, and which will be described in greater detail below. Protrusions 104a and 104b may be integrally formed with proximal connectors 100f, 100g.

For example, an operator may be guided by an external marker provided with device 100, and apply a torque that is transferred to device 100 and that causes it to rotate, thereby aligning central ridge 100c with the anterior inter-lobar groove of the prostatic urethra.

Device 100 may be integrally formed, and may be made of a suitably flexible material, such as wire or cut foil made of a super-elastic alloy such as Nitinol. Alternatively, device may be made of a super-elastic polymer or biodegradable polymer.

This memory-retaining flexibility may allow distal connectors 100d and 100e and proximal connectors 100f and 100g to bend in a manner that decreases the distance between ridges 100a, 100b and 100c, thereby compressing device 100 to enable its insertion into the prostatic urethra. Additionally, distal connectors 100d and 100e and proximal connectors 100f and 100g may be normally unbent, and may revert to their normally unbent configuration upon deployment within the prostatic urethra, thereby increasing the distance between ridges 100a, 100b and 100c and expanding device 100 to enable dilating the prostatic urethra.

Figure 1C:
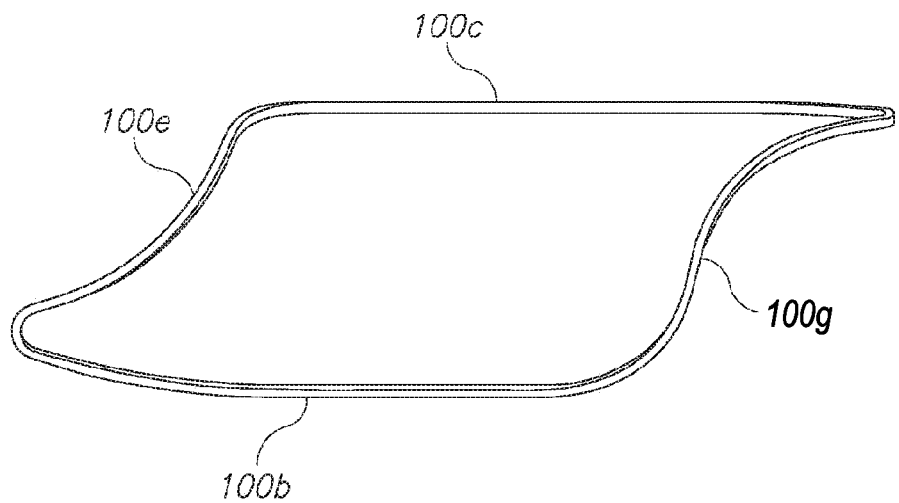
FIG. 1C shows a profile view of the device of FIG. 1A, according to an embodiment.

Reference is made to FIG. 1C, which shows a profile view of the device of FIGS. 1A-B, according to an embodiment. The closed form that is formed by peripheral ridge 100b, central ridge 100c, distal connector 100e, and proximal connector 100g resembles a 'butterfly wing'. An identical and symmetric butterfly wing (not shown) is formed by peripheral ridge 100a, central ridge 100c, distal connector 100d, and proximal connector 100f.

Figure 1D:
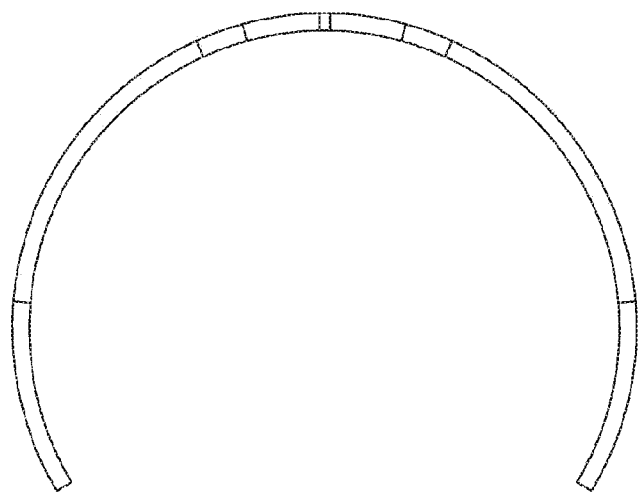
FIG. 1D shows a frontal view of the device of FIG. 1A, according to an embodiment.

Reference is now made to FIG. 1D, which shows a frontal view of the device of FIGS. 1A-B, according to an embodiment. When normally-open, S-shaped distal connectors 100d, 100e, comprising a distal end of device 100, may be configured to span an arc, such as a portion of a circle to dilate the prostatic urethra at the bladder neck.

In one embodiment, the shape of the device in the normally-open configuration may reside within the delimiting surface of a longitudinally oriented tube, such as a free-form longitudinally-oriented lumen. The shape of the lumen may be a cylinder, prism, or trunk-conical shape, to name a few, and may comprise a combination of shapes. For example, the lumen may have a cylindrical shape at the tubular ends, and a triangular prism shape at the midsection. The profile, or cross section of such shape may be circular ovoid, triangular, and may be uniform or may change in size and/or shape along the axial length. In the example given above, the cross-section at the ends of the open device may be circular due to the normally-open circular arc-shape of connector pairs 100d, 100e, and 100f, 100g, whereas the cross-section at the middle of the device may be triangular due to the three ridges 100d, 100e, 100c that are 'pulled apart' by the normally open connectors. The device may have a varying cross-sectional size. For example, a portion of the device may reside within a fraction, such as 50%, 66%, or 75% of the longitudinally oriented tube.

Similarly, in the normally-open configuration, S-shaped proximally connectors 100f, 100g, comprising a proximal end of device 100 may be configured to reside within the circular delimiting surface of a cylinder to dilate the prostatic urethra at the proximal end of device 100.

The device may be shaped for residing within the prostate urethra and for positioning on the longitudinal axis between the external sphincter of the urethra distally and the bladder neck proximally.

In an embodiment, connectors 100d, 100e with ridge 100c may, in the normally-open configuration, may create an arc that exerts a lateral force on the lateral prostate lobes and dilates the prostate. Similarly, connectors 100f, 100g with 100c may create another arc that exerts a lateral force on the lateral prostate lobes and may dilate the prostate at a region situated distally. Thus, the device may provide two or more arcs that each exert a lateral force on a different region of the lateral prostate lobes.

In another embodiment additional connectors (not shown), similar and substantially parallel to connectors 100d, 100e, 100f, and 100g, may be provided to laterally connect each peripheral ridge 100a, 100b, to the central ridge 100c at a point on each ridge that lies between the distal and proximal ends of the peripheral and central ridges 100a, 100b, 100c, such as at a midpoint along the ridge. The distance along the long axis of the device between any such pair of connectors may be between 0.5 cm to 3 cm, or more explicitly between 1 cm to 2 cm. The shape of the device in the normally-open configuration may reside within the delimiting surface of an longitudinally oriented tube, such as a free-form longitudinally-oriented lumen.

In an embodiment, the length of the device may range between 1 cm to 7 cm. There may be different sizes suitable for different lengths of prostate urethra.

In an embodiment, the diameter of the expanded device may be between 10 mm to 30 mm, and more explicitly between 15 mm and 25 mm.

In an embodiment, the device may be compressed to a minimal diameter of 0.5 mm to 3 mm and more explicitly of 1 mm to 2 mm.

In an embodiment, in case of a Nitinol device, the wire or ribs size may range from 0.2 to 0.8 mm and more explicitly between 0.3 mm to 0.6 mm.

In an embodiment, the dilating action of the device on the prostate urethra may be performed by the radial outward force exerted by the longitudinally oriented ridges on the prostate grooves and by an additional force exercised on the lateral lobes by the arc formed by the connection of components 100d, 100c, 100e, and the arc formed by the connection of components 100f, 100c, 100g.

In an embodiment, the components of the device, such as the ridges and connectors, or alternatively, the dilating means and connecting ridges of the device may be configured to maintain intimate contact with the mucosa of the prostate urethra when the device is in the open configuration.

Alternatively, the arcs formed by connectors 100d, 100e, 100f, and 100g of device 100 may comprise at least two dilating means of the prostate urethra. Connectors 100d, 100e, 100f, and 100g may be connected with longitudinally oriented ridges 100a, 100b, and 100c that may be configured to fix the dilating means in place within the prostate urethra and prevent their movement or dislodgement.

In one embodiment, any of connectors 100d, 100e, 100f, and 100g may comprise closed rings, and any of connecting ridges may have an oblique or sinusoidal orientation.

Figure 2B:
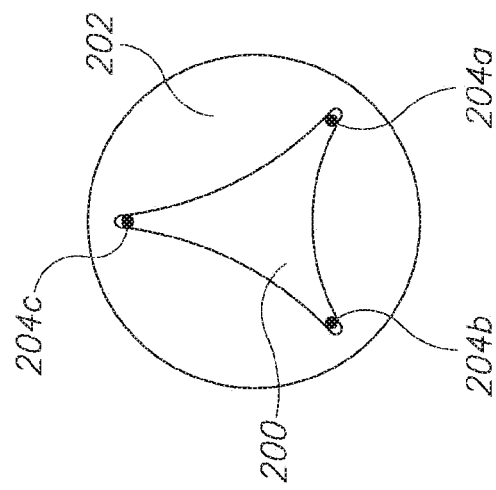
FIGS. 2A-B, together show an exemplary deployment of a device for dilating a prostatic urethra, according to an embodiment.
Figure 2A:
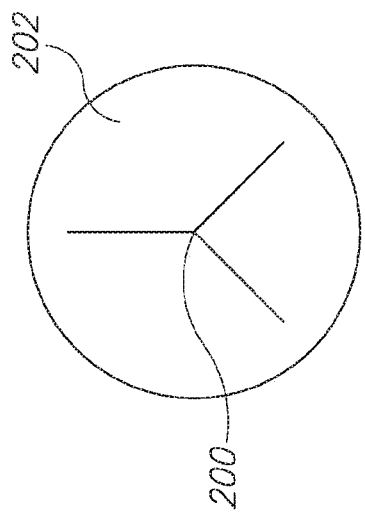
Figure 3A:
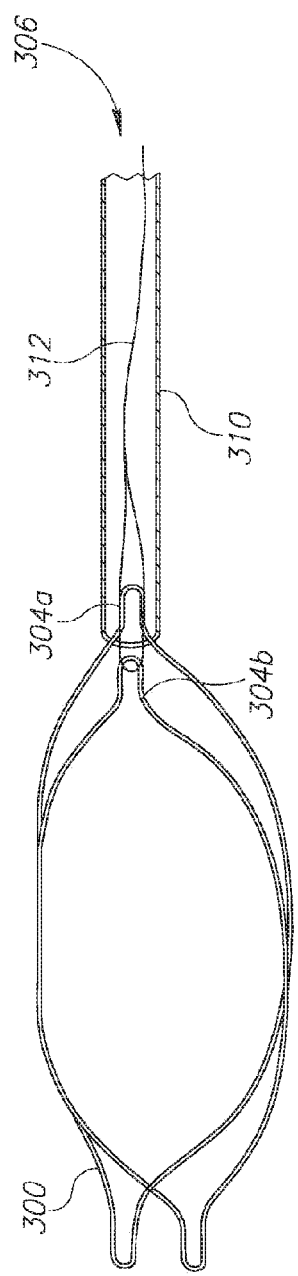
FIGS. 3A-B together illustrate a deployment apparatus for a dilating device for the prostatic urethra, in accordance with an embodiment.
Figure 3B:
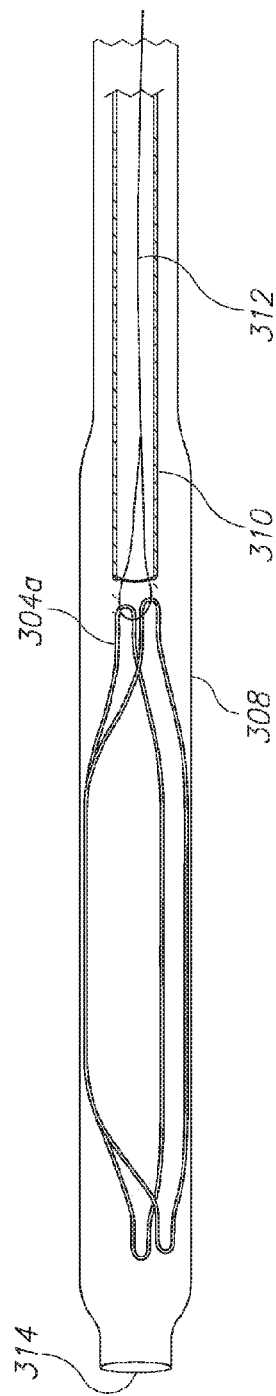

Reference is now made to FIGS. 2A-B, which together show an exemplary deployment of a device for dilating a prostatic urethra, according to an embodiment. FIG. 3A shows a cross-section of prostatic urethra 200 that is obstructed by an enlarged prostate 202. FIG. 3B shows the cross-section of the prostatic urethra of FIG. 3A upon deploying a dilating device, in accordance with an embodiment of the invention. The three laterally connected ridges of the device that are illustrated at a midsection view along the axially oriented device and labeled as points 204a, 204b, and 204c, are shown in the normally-open configuration and engaged within the grooves of prostatic urethra 200, thereby dilating urethra 200 to allow a free passage of fluid therethrough.

Reference is now made to FIGS. 3A-B which together illustrate an apparatus for deploying a dilating device for the prostatic urethra, in accordance with an embodiment. FIG. 3A shows a dilating device 300 in the normally-open configuration such as after deployment, and FIG. 3B shows device 300 in the compressed configuration while housed within a deployment lumen 308, prior to deployment. The apparatus for deployment and the dilating device may be jointly referred to as a "kit".

Figure 4A:
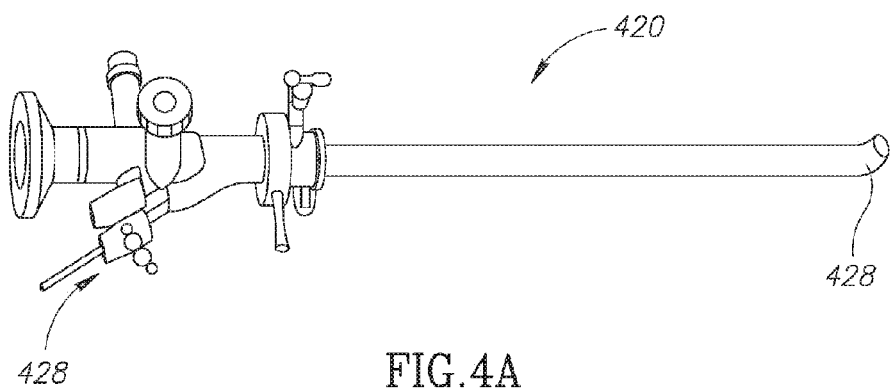
FIGS. 4A-B show a cystoscope configured to deploy a dilating device for the prostatic urethra, in accordance with an embodiment.

Turning to FIG. 3B, to deploy device 300, deployment lumen 308 may be retracted relative to device 300 to expose device 300 from the distal end 314 of lumen 308, allowing device 300 to protrude from lumen 308 and expand to its normally-open configuration, as shown in FIG. 4A. Upon protruding from lumen 308 and during the expansion of device 300, the ridges of device 300 may engage with the grooves of the prostatic urethra and cause it to dilate, as described above. To reposition device 300 within the prostatic urethra after its exposure from lumen 308, device 300 may be retracted relative to lumen 308, such as by pulling a string 312 that is releasably attached to device 300 and that is exposed from a proximal end of deployment lumen 308. The distal opening 314 of lumen 308 may press on the expanded ridges of device 300, causing device 300 to compress and allowing its retreat into lumen 308 where it may be housed for subsequent redeployment.

The retraction of either deployment lumen 308 or device 300 in relation to each other may be performed mechanically by a practitioner, such as via a work channel of a cystoscope, and which will be described in greater detail below.

Dilating device 300 may be provided with one or more proximally disposed protrusions 304a and 304b that are that may be integrally formed with the proximal end of device 300 and that are configured to releasably connect device 300 to an alignment mechanism 306 that is configured for being housed within deployment lumen 308.

Alignment mechanism 306 may comprise an alignment lumen 310 concentrically housed within deployment lumen 308, as well as releasable string 312. String 312 may loop through protrusions 304a and 304b of device 300 and may run through alignment lumen 310 and may be exposed from a proximal end of alignment lumen 310 for subsequent removal upon deployment of device 300. Device 300 may be configured for alignment within the prostatic urethra via a torque that is transferred from alignment mechanism 306 to device 300. For example, an operator may rotate alignment lumen 310 to align alignment lumen 310 with an externally provided alignment mark, thereby applying a torque to alignment lumen 310 that is transferred by alignment mechanism 306 to device 300 and causes device 300 to be aligned within the prostatic urethra.

Figure 4B:
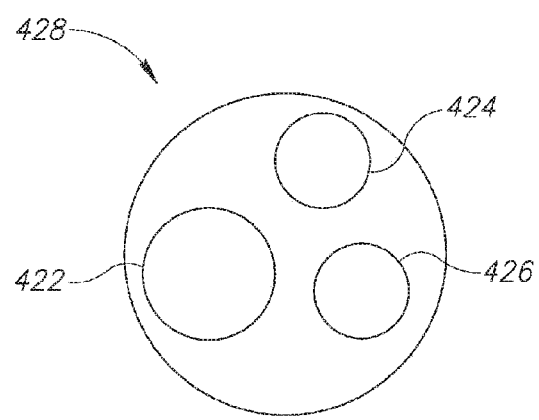

Alternatively, referring to FIGS. 4A-B a cystoscope 420 disposed with a work channel 422 may be used for deploying device 300 of FIGS. 3A-B from the distal end 428 of cystoscope 420. Device 300 housed within deployment lumen 308 and optionally with alignment lumen 310 may be inserted into work channel 422. The deployment and alignment of device 300 may be controlled from a proximal end 428 of work channel 422.

In an embodiment, cystoscope 420 may be provided with a fluid delivery lumen and a balloon (not shown) that are configured to deliver a fluid to inflate the patient's bladder. The device may be configured for delivery into the inflated bladder, where it may be extracted from the deployment lumen to expand within the bladder, and then retracted for final deployment within the prostate urethra.

Reference is made to to FIG. 4B which shows a close-up view of distal end 428 of cystoscope 420, a camera 424 and illuminator 426 provided with cystoscope 420 may be utilized, in an embodiment, for aligning and deploying device 300 using conventional techniques. Deployment lumen 308 housing device 300 and alignment mechanism 306, and optionally the fluid delivery lumen and balloon, may be inserted into work channel 422 of cystoscope 420 and may be manipulated from a proximal end 428 of work channel 422 to deploy device 300 within the prostatic urethra. The patient's bladder may be filled via the fluid delivery lumen and balloon, allowing deployment of device 300 within the prostatic urethra via the bladder.

Figure 5:
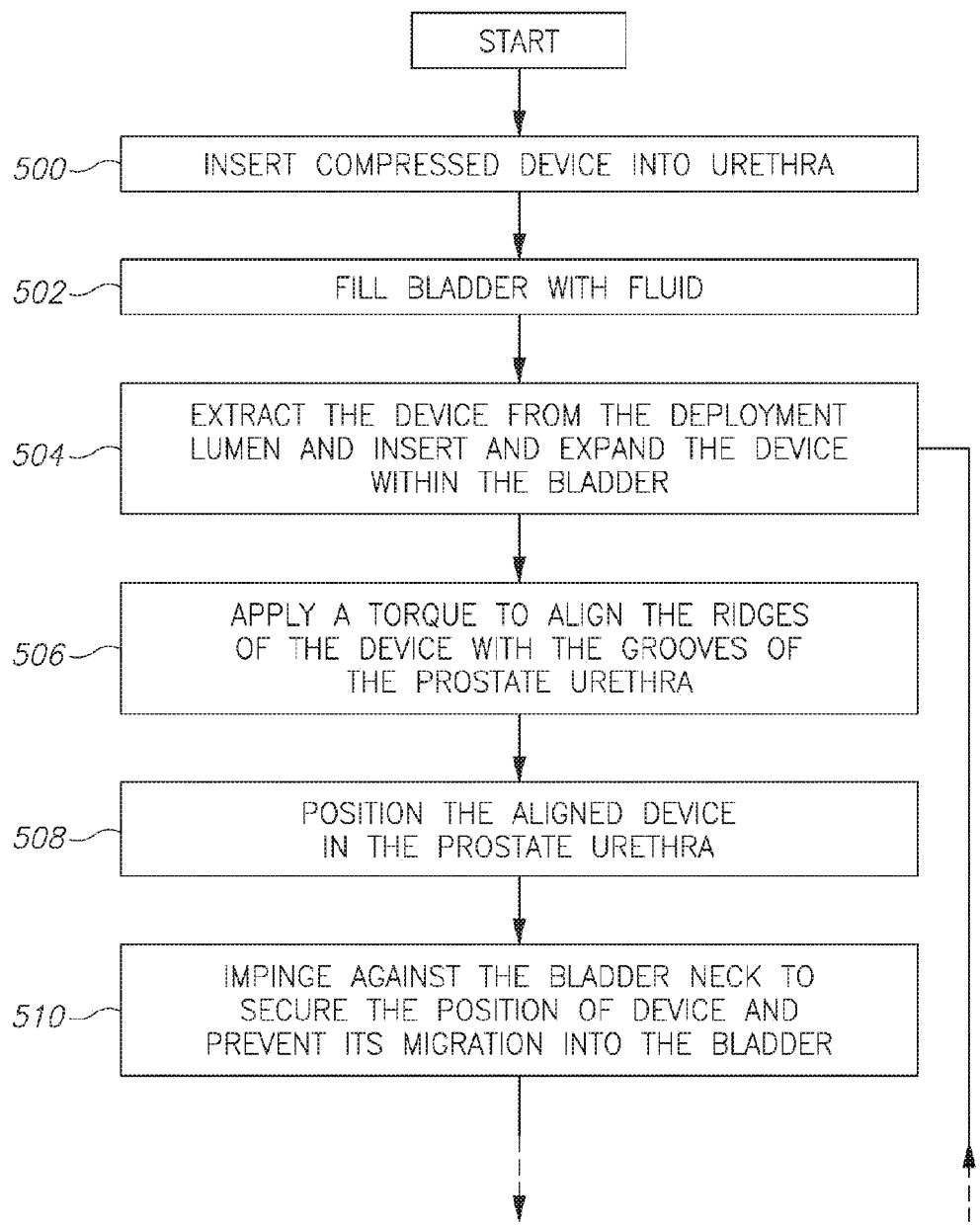
FIG. 5 shows a flowchart of a method for dilating the prostatic urethra, according to an embodiment.

Reference is now made to FIG. 5 which is a flowchart of a method for deploying a dilating device into a prostatic urethra.

The laterally compressed dilating device may by inserted into the urethra of a patient via a deployment lumen that is releasably connected to the device (Step 500). The patient's bladder may be filled according to conventional techniques, such as via a fluid delivery lumen disposed with a balloon (Step 502). The device may be extracted from the deployment lumen and inserted into the urinary bladder, such as by retracting the deployment lumen relative to the device, and, upon exiting from the deployment lumen, the dilating device may expand to a normally-open configuration in the partially filled urinary bladder of the patient (Step 504). A torque may be applied to align the device via an alignment mechanism connected to the device, such as by rotating an alignment lumen of the alignment mechanism and transferring the torque to the device, where alignment may comprise aligning a central ridge of the device for engaging with the anterior inter-lobar groove of the prostatic urethra and aligning two peripheral ridges of the device to each engage with a different postero-lateral groove of the prostatic urethra (Step 506). The application of the torque may be guided via a cytoscope, or alternatively, via an external mark indicating that the device is aligned.

The aligned device may be positioned in the prostate urethra, such as by pulling on the deployment mechanism to draw the device in from the bladder into the prostate urethra (Step 508). Two protrusions disposed at the distal end of the device may be caused to impinge against the postero-lateral side of the bladder neck, thereby securing the position of the device, and preventing a migration of the device into the urinary bladder (Step 510). The device, thus deployed and aligned within the prostatic urethra, may exert an outwards radial force that pushes the inter-lobar grooves of the urethra outwards, and dilate the urethra (Step 512).

If the positioning or alignment of the device is incorrect, the device may be retracted relative to the deployment lumen, causing the device to laterally compress and retreat within the deployment lumen (Step 514). The retreated device may be repositioned or realigned within the prostatic urethra and redeployed (Steps 504-512). If the positioning and alignment of the device is correct, The device may be disconnected from the deployment and alignment lumens (Step 518), such as by removing a string that releasably connects the device to the alignment lumen.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall therebetween.

What is claimed is:

1. A dilating device for dilating a prostatic urethra, the device comprising:
    a central ridge longitudinally oriented and positioned on an anterior peripheral edge of the dilating device to engage an anterior inter-lobar groove of the prostatic urethra; and
    a first closed form positioned on a first side of the central ridge including a first peripheral ridge; said first peripheral ridge forming a postero-lateral edge of the device on said first side of the central ridge;
    a second closed form symmetrically positioned on a second side of the central ridge laterally opposite said first side; said second closed form including a postero-lateral second peripheral ridge; said second peripheral ridge forming a postero-lateral edge of the device on said second side of the central ridge;
    wherein the dilating device is configured to be laterally expandable in the prostatic urethra to a normally-open configuration wherein
    said first peripheral ridge is extended away from said central ridge by
        a first distal connector connecting a distal portion of the first peripheral ridge to a distal portion of the central ridge and
        a first proximal connector connecting a proximal portion of said first peripheral ridge to a proximal portion of the central ridge, and
    said second peripheral ridge extended away from said central ridge by
        a second distal connector connecting a distal portion of the second peripheral ridge to said distal portion of the central ridge and
        a second proximal connector connecting a proximal portion of said second peripheral ridge to said proximal portion of the central ridge;
    such that said first distal connector and said second distal connector form lateral edges of a distal cross section of the dilating device, the lateral edges connected on their anterior ends to said central ridge of the device;
    wherein in said normally-open configuration, a posterior side of said dilating device is open; and said first peripheral ridge delimits a first edge of the posterior opening of the dilating device and said second peripheral ridge delimits a second edge of the posterior opening of the dilating device on an opposite lateral side of said posterior opening from said first edge;
    wherein each of said first closed form and said second closed form is laterally compressible to a compressed configuration configured for insertion into the prostatic urethra.

2. The device of claim 1, wherein each of said first closed form and said second closed form comprises a lengthwise oriented ovoid loop in the normally-open configuration.

3. The device of claim 1, wherein a first plane including the central ridge and said first peripheral ridge is substantially non-parallel to a second plane including the central ridge and said second peripheral ridge in the normally-open configuration.

4. The device of claim 1, wherein each distal connector is substantially S-shaped, in a profile view of the normally-open configuration, configured to fit a bladder neck and for dilating the prostatic urethra at said bladder neck.

5. The device of claim 1, wherein each of said first and second proximal connectors is substantially S-shaped, in a profile view of the normally-open configuration.

6. The device of claim 1, wherein each of said first distal connector and said second distal connector includes on a posterior portion thereof a respective distally positioned protrusion protruding distal to a distal end of said central ridge and configured to impinge against a postero-lateral side of a neck of a urinary bladder, thereby preventing a migration of the device into the urinary bladder.

7. The device of claim 1, wherein said first peripheral ridge and said second peripheral ridge include longitudinally oriented structure composed of at least one of wire, cut foil, super-elastic alloy, or super-elastic polymer.

8. The dilating device of claim 1, wherein said first closed form and said second closed form branch out from the central ridge to form an open sided V-shaped cross section.

9. The dilating device of claim 1, wherein in said compressed configuration, the device is configured to reside within a cystoscope.

10. The dilating device of claim 1, wherein in said normally-open configuration said first peripheral ridge and said second peripheral ridge are configured to engage and exert outwards force on opposing posterolateral grooves of the prostatic urethra to dilate the prostatic urethra.

11. The dilating device of claim 1, wherein said first and second distal connectors have an arced shape that arcs laterally outward between said central ridge and first and second peripheral ridges respectively, and wherein said arced shape is configured to exert a lateral outward force on said prostatic urethra.

12. The dilating device of claim 11, wherein in said normally-open configuration, said cross section of a distal portion of the device is curved and a cross section of a central portion of the device is triangular.

13. The device of claim 1, wherein said central ridge includes a longitudinally oriented structure composed of at least one of wire, cut foil, super-elastic alloy, or super-elastic polymer.

14. The device of claim 1, wherein said first and second peripheral ridges extend distally further than said central ridge.

15. The device of claim 1, wherein said first distal connector connects a distal end of the first peripheral ridge to a distal end of the central ridge.

16. The device of claim 1, wherein said second distal connector connects a distal end of the second peripheral ridge to said distal end of the central ridge.

* * * * *